United States Patent
Prosise et al.

(10) Patent No.: US 7,124,483 B2
(45) Date of Patent: Oct. 24, 2006

(54) PROCESS FOR PRODUCING STABILIZED TAMPONS

(75) Inventors: Robert Lawrence Prosise, Cincinnati, OH (US); Robert Clark Avery, Jr., Mason, OH (US); Andrew Lloyd Bouthilet, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 235 days.

(21) Appl. No.: 10/435,822

(22) Filed: May 12, 2003

(65) Prior Publication Data

US 2004/0226152 A1 Nov. 18, 2004

(51) Int. Cl.
*A61F 13/20* (2006.01)

(52) U.S. Cl. ...................................................... 28/118

(58) Field of Classification Search ................... 28/118, 28/119, 120, 116, 122, 121, 123, 165, 282, 28/283; 604/904, 385.17, 385.18, 379, 380, 604/286; 264/413, 443, 479, 489, 486, 319, 264/345, 402–405, 294, 320, 325, 327; 156/62.2, 156/180, 166, 167, 285, 311
See application file for complete search history.

(56) References Cited

U.S. PATENT DOCUMENTS

| | | | | |
|---|---|---|---|---|
| 2,077,231 A | * | 4/1937 | Fourness et al. | ............... 28/118 |
| 2,976,579 A | | 3/1961 | Rabell | |
| 3,013,558 A | * | 12/1961 | Leupold | ...................... 604/377 |
| 3,095,343 A | * | 6/1963 | Berger | ........................ 156/180 |
| 3,658,626 A | * | 4/1972 | Berger et al. | ................ 156/441 |
| 3,674,025 A | * | 7/1972 | Bleuer | .......................... 604/12 |
| 3,738,364 A | * | 6/1973 | Brien et al. | ................... 604/375 |
| 3,819,435 A | * | 6/1974 | Roberts et al. | ............. 156/62.2 |
| 3,874,032 A | | 4/1975 | Simon | |
| 4,081,884 A | * | 4/1978 | Johst et al. | ..................... 28/119 |
| 4,326,527 A | | 4/1982 | Wollangk | |
| 5,084,038 A | | 1/1992 | Sheldon et al. | |
| 5,153,971 A | * | 10/1992 | Van Iten | ........................ 28/118 |
| 5,161,283 A | * | 11/1992 | Hansen | ......................... 19/148 |
| 5,382,153 A | | 1/1995 | Nettelnstroth | |
| 6,003,216 A | * | 12/1999 | Hull et al. | ..................... 28/119 |
| 2003/0233742 A1 | * | 12/2003 | Jones et al. | .................... 28/118 |

FOREIGN PATENT DOCUMENTS

DE        3815506      * 11/1989

OTHER PUBLICATIONS

PCT International Search Report dated Dec. 10, 2004.

* cited by examiner

*Primary Examiner*—A. Vanatta
(74) *Attorney, Agent, or Firm*—James E. Oehlenschlager; Bridget Ammons; David M. Weirich

(57) ABSTRACT

The invention relates to a process for providing stabilized compressed tampon pledgets. The process includes the steps of providing a compressed tampon pledget and forcing gas through the compressed absorbent pledget. In some embodiments, the process may occur in the presence of moisture, the moisture required comes from either the fibers of the material that comprises the tampon pledget and/or from the humidified gas that is introduced. The process may include the steps of heating and/or humidifying the gas introduced during the process. The gas may be forced through the compressed tampon pledget intermittently during the process. The tampon pledget may be maintained within a permeable mold during the process.

20 Claims, 3 Drawing Sheets

PROCESS FOR PRODUCING STABILIZED TAMPONS

FIELD OF THE INVENTION

The invention relates to a process for providing stabilized compressed tampon pledgets.

BACKGROUND OF THE INVENTION

It is well known in the art, that during the production of tampons, tampon pledgets have a tendency to re-expand to their original dimensions after a compression step. Heat setting has been utilized to overcome this tendency. Heat setting is the application of heat to a compressed tampon pledget designed to "set" or stabilize the tampon in the compressed state. Currently, tampons are set or stabilized by either conductive heating or microwave heating, both of which have drawbacks.

Commonly, conductive heating methods do not uniformly stabilize the tampon and may result in the alteration of absorbent qualities in the outer layer of the tampon because the dense, compacted material on the outside of the tampon dries more quickly than the inside. Conductive heating methods may also be time intensive because the air inside the tampon must be heated to dry the fibers via conduction from outside the pledget to the inside. As well, high temperatures that may decrease cycle times cannot be utilized in conductive heating methods because these temperatures may be above the melting point of tampon overwraps resulting in a melted product.

While microwave heating can be a faster method of stabilizing tampons than conductive heating, microwave heating does not uniformly stabilize tampons and may create "hot spots" within the tampon and may also melt the overwrap of the tampon. As well, only a small fraction of the outputted energy in microwave heating actually goes into stabilizing the tampon, thus energy costs of this method are relatively high.

The superior design of the present invention provides an efficient process for uniformly stabilizing a compressed tampon pledget by forcing a gas through a compressed tampon pledget. The process of the present invention has the benefit of more consistent stabilization while at the same time being less dependent on incoming moisture.

BACKGROUND ART

U.S. Pat. No. 4,326,527 issued to Wollangk, et al. relates to microwave heat setting of tampons.

SUMMARY OF THE INVENTION

The invention relates to a process for providing stabilized compressed tampon pledgets. The process comprises the steps of providing a compressed tampon pledget and forcing a gas through the compressed absorbent pledget.

BRIEF DESCRIPTION OF THE DRAWINGS

While the specification concludes with claims particularly pointing out and distinctly claiming the subject matter that is regarded as forming the present invention, it is believed that the invention will be better understood from the following description taken in conjunction with the accompanying Figures, in which:

DETAILED DESCRIPTION OF THE INVENTION

As used herein, "compression" refers to the process of pressing, squeezing, compacting or otherwise manipulating the size, shape, and/or volume of a material to obtain a tampon having a vaginally insertable shape. The term "compressed" refers to the state of a material or materials subsequent to compression. Conversely, the term "uncompressed" refers to the state of a material or materials prior to compression. The term "compressible" is the ability of a material to undergo compression.

The term "joined" or "attached," as used herein, encompasses configurations in which a first element is directly secured to a second element by affixing the first element directly to the second element; configurations in which the first element is indirectly secured to the second element by affixing the first element to intermediate member(s) which in turn are affixed to the second element; and configurations in which the first element is integral with the second element; i.e., the first element is essentially part of the second element.

Figure 1:
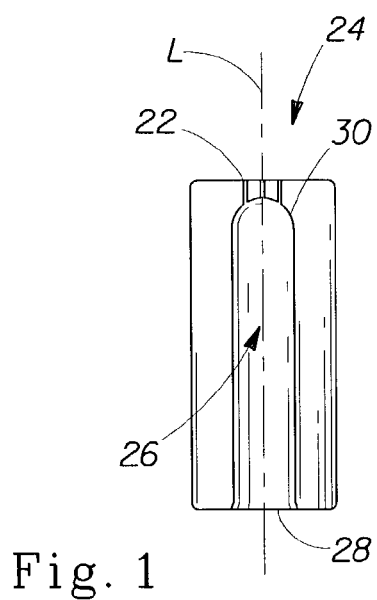
FIG. 1. is a cross section of a unitary embodiment of the permeable mold with pores located axially along the mold.
Figure 2:
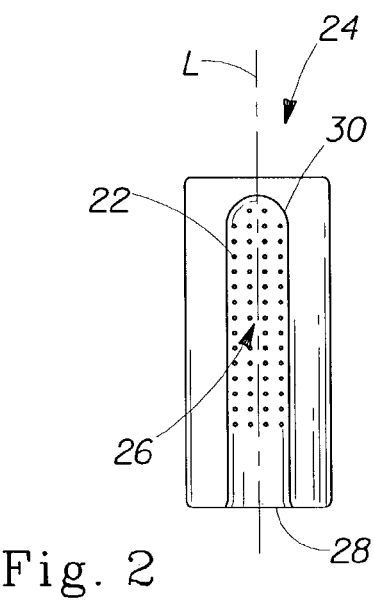
FIG. 2 is a cross section of a unitary embodiment of the permeable mold with pores located radially along the mold.

As used herein, "mold" refers to a structure for shaping a tampon pledget during compression and/or retaining the shape for a compressed tampon pledget subsequent to compression during the stabilization process. Molds have an inner surface defining an inner cavity and an outer surface. The inner cavity is structured to define or mirror the shape of the compressed absorbent tampon pledget. Thus, in some embodiments the tampon pledget conforms to the shape of the inner cavity of the mold by a restraining force to result in a self-sustaining shape and is retained in the inner cavity during the stabilization process. In other embodiments, the mold retains the shape of the compressed tampon pledget during the stabilization process. The inner cavity may be profiled to achieve any shape known in the art including, but not limited to, cylindrical, rectangular, triangular, trapezoidal, semi-circular, hourglass, serpentine or other suitable shapes. The outer surface of the mold is the surface external to the inner surface and can be profiled or shaped in any manner, such as, rectangular, cylindrical or oblong. The mold may comprise one or more members. One mold used in the present invention may be a unitary mold, comprising one member, as shown in FIGS. 1 and 2, or "split cavity mold" as shown in FIG. 3, FIG. 4, FIG. 5, FIG. 6, and FIG. 7. Split cavity molds may be preferred when producing shaped tampons, such as those disclosed in U.S. patent application Ser. No. 10/150050 entitled "Substantially Serpentine Shaped Tampon," and U.S. patent application Ser. No. 10/150055, entitled "Shaped Tampon," both filed on Mar. 18, 2002. Whereas unitary molds may be used for less complex shapes such as cylindrical or substantial cylindrical.

The term "permeable," as used herein, refers to the ability of a material to allow the spread or infusion of a gas through the material's composition. A material may be permeable due to its composition or the material may be fabricated from impermeable material then modified to become permeable, either chemically, mechanically, or electrically, such as, for example by acid etching, drilling, or aperturing.

As used herein the terms "pledget" or "tampon pledget" are intended to be interchangeable and refer to a construction of absorbent material prior to the compression of such construction into a tampon.

The term "pores," as used herein, refers to small openings or interstices that connect the inner surface of the mold with the outer surface of the mold admitting the passage and infusion of gases into and through a compressed tampon pledget contained within the inner cavity of the mold.

As used herein, "self-sustaining" is a measure of the degree or sufficiency to which the tampon retains its compressed form after stabilization such that in the subsequent to the absence of external forces, the resulting tampon will tend to retain its vaginally insertable shape and size. For tampons, it is found that control of the level of moisture within the tampon is a factor for helping the tampon to retain its shape subsequent the absence of the external compression forces. It will be understood by one of skill in the art that this self-sustaining form need not, and preferably does not persist during actual use of the tampon. That is, once the tampon is inserted into the vagina or other body cavity and begins to acquire fluid, the tampon will begin to expand and may lose its self-sustaining form.

The term "shaped tampons," as used herein, refers to compressed tampon pledgets having either a substantially serpentine shape, a "undercut" or "waist". The phrase "substantially serpentine" refers to a non-linear dimension between any two points spaced at least about 5 mm apart. The term "undercut" refers to tampons having a protuberance or indentation that impedes the withdrawal from a unitary mold. For example, shaped tampons may be hourglass shaped having at least one perimeter in the center of the tampon or "waist" that is less than both an insertion end perimeter and a withdrawal end perimeter.

As used herein, the term "split cavity mold" is a mold comprised of two or more members that when brought together complete the inner cavity of the mold. Each member of the split cavity mold comprises at least a portion of the inner surface that when brought together or closed completes the mold structure. The split cavity mold is designed such that at least two or more of the mold members can be at least partially separated, if not fully separated, typically after the tampon has acquired a self-sustaining shape, to expand the cavity volume circumscribed by the inner surface(s) thus permitting the easier removal of the tampon from the mold. Partial separation can occur when only a portion of two mold members are separated while other portions of the two mold members remain in contact. Where each member's inner surface portion joins the inner surface portion of another member, those points of adjacency can define a straight line, a curve, or another seam of any convoluted intersection or seam of any regular or irregular form. The elements of the split cavity in some embodiments may be held in appropriate position relative to each other by linking elements of any form including bars, rods, linked cams, chains, cables, wires, wedges, screws, etc.

The term "stabilized," as used herein, refers to a tampon in a self-sustaining state wherein it has overcome the natural tendency to re-expand to the original size, shape and volume of the absorbent material and overwrap, which comprise the tampon pledget.

As used herein the term "tampon," refers to any type of absorbent structure that is inserted into the vaginal canal or other body cavities for the absorption of fluid therefrom, to aid in wound healing, or for the delivery of active materials, such as medicaments, or moisture. The tampon may be compressed into a generally cylindrical configuration in the radial direction, axially along the longitudinal axis or in both the radial and axial directions. While the tampon may be compressed into a substantially cylindrical configuration, other shapes are possible. These may include shapes having a cross section that may be described as rectangular, triangular, trapezoidal, semi-circular, hourglass, serpentine, or other suitable shapes. Tampons have an insertion end, withdrawal end, a length, a width, a longitudinal axis and a radial axis. The tampon's length can be measured from the insertion end to the withdrawal end along the longitudinal axis. A typical compressed tampon for human use is 30–60 mm in length. A tampon may be straight or non-linear in shape, such as curved along the longitudinal axis. A typical compressed tampon is 8–20 mm wide. The width of a tampon, unless otherwise stated in the specification, corresponds to the length across the largest cylindrical cross-section, along the length of the tampon.

The term "vaginal cavity," "within the vagina," and "vaginal interior," as used herein, are intended to be synonymous and refer to the internal genitalia of the mammalian female in the pudendal region of the body. The term "vaginal cavity" as used herein is intended to refer to the space located between the introitus of the vagina (sometimes referred to as the sphincter of the vagina or hymeneal ring,) and the cervix. The terms "vaginal cavity," "within the vagina" and "vaginal interior," do not include the interlabial space, the floor of vestibule or the externally visible genitalia.

As used herein, "cm" is centimeter, "g" is grams, "g/m$^2$" is grams per meter squared, "L" is liters, "L/s" is liters per second, "mL" is milliliters", "mm" is millimeters, "min" is minutes, "rpm" rate per minute, and "s" is seconds.

FIG. 1 and FIG. 2 show cross sections of a unitary embodiment of the permeable mold with a longitudinal axis L. The structure of the unitary mold 24 is a one piece mold so arranged as to define a space or inner cavity 26 for shaping a tampon pledget 20 (not shown) during compression and/or retaining the shape for a compressed tampon pledget 20 subsequent to compression during the stabilization process. The inner cavity 26 has an open proximal end 28 and a closed distal end 30. In the unitary embodiments of the permeable mold, the open proximal end 28 is used for both an ingress port wherewith the tampon pledget 20 is introduced into the inner cavity 26 and an egress port wherewith the tampon pledget 20 can be extracted from the inner cavity 26. In the embodiment shown in FIG. 1, the unitary mold 24 has pores 22 located axially along the unitary mold 24, the pores 22 are shown at the closed distal end 30. As shown in FIG. 2, the unitary mold 24 has pores 22 located radially along the unitary mold 24.

Figure 3:
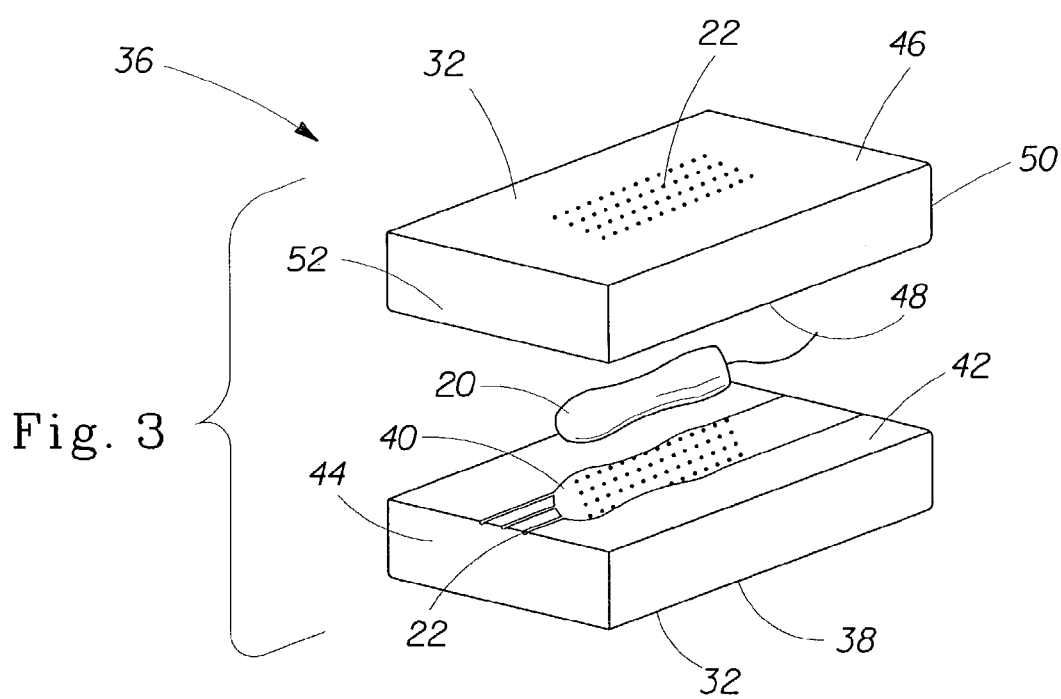
FIG. 3 is an exploded view of the split cavity mold with the compressed tampon pledget positioned between the first split cavity mold member and the second split cavity mold member.

FIG. 3 shows an exploded view of the split cavity mold 36 with the compressed tampon pledget 20 positioned between the first split cavity mold member 38 and the second split cavity mold member 46. The first split cavity mold member 38 and second split cavity mold member 46 are combined to form a split cavity mold 36. The first split cavity mold member 38 has a first inner surface 40 and an outer mold surface 32. The second split cavity mold member 46 is substantially similar, if not a mirror image or not identical in size, shape, and dimension to the first split cavity mold member 28 and has a second inner surface 48 and an outer mold surface 32. The first split cavity mold member 38 and the second split cavity mold member 46 are configured such that the first end 42 and the second end 44 of the first split cavity mold member 38 corresponds to the first end 50 and the second end 52 of the second split cavity mold member 46, such that, the first inner surface 40 and the second inner surface 48 face toward each other. These inner surfaces make up an inner cavity that is the desired shape of the compressed tampon pledget 20. In the embodiment shown, both the first split cavity mold member 38 and the second split cavity mold member 46 have pores 22 located axially and radially along the mold.

The mold can be constructed from permeable materials or can be fabricated from impermeable or permeable materials then modified either mechanically, chemically, or electrically to become permeable. Materials for the mold may include metals, polymers and/or composites. Embodiments of the mold that are comprised of metals may include steel, stainless steel, copper, brass, titanium, alloys, aluminum, anodized aluminum, titanium and combinations thereof. Embodiments of the mold that are comprised of polymers may include TEFLON® (E.I du Pont de Nemours and Company), polyethylene, polypropylene, polyester, polyolefins, polycarbonates, nylons, polyvinyl chloride, and mixtures thereof. One embodiment of a mold may be made of DELRIN® made by DuPont Plastics (Wilmington, Del. U.S.A.). Embodiments of the mold that are comprised of composites may include carbon fibers and blends of metal, epoxy, ceramic and polymer blends. Other examples of suitable materials for the mold are foamed metals or plastics. The mold may be made of aluminium and epoxy porous aggregate, such as METAPOR BF100A1, available from Portec Ltd, Switzerland. Pores 22, interstices, or pathways can be mechanically produced in the above materials by any mechanical operation known in the art including, but not limited to, operations such as drilling, milling, punching, casting, injection molding, and the like. Chemical modification techniques may include acid etching. Electrical modification techniques may include electrical discharge machining.

In several embodiments used with the process of the present invention, the tampon pledget is maintained within a mold that comprises at least one pore 22 along the length of the mold. The mold may have a plurality of pores 22 in some embodiments. The pores 22 can be on any location on the mold. In embodiments in which the mold is cylindrical, the pores 22 may be located radially, axially, or both radially and axially. These pores 22 may be macroscopic, microscopic or sub-microscopic. In some embodiments, the pores 22 may range in diameter from about 0.2 mm to about 1.5 mm.

The process of the present invention may be used for stabilizing any type of tampon known in the art including but not limited the tampon disclosed in U.S. Pat. No. 6,258,075 issued to Taylor, et al on Jul. 10, 2001 and the shaped tampons disclosed in U.S. patent application Ser. No. 10/150050 entitled "Substantially Serpentine Shaped Tampon," and U.S. patent application Ser. No. 10/150055, entitled "Shaped Tampon," both currently pending, commonly assigned, and filed on Mar. 18, 2002.

The absorbent material that comprises the compressed tampon pledgets 20 may be constructed from a wide variety of liquid-absorbing materials commonly used in absorbent articles. Such materials include but are not limited to rayon (such as GALAXY Rayon SARILLE L rayon both available from Acordis Fibers Ltd., of Hollywall, England), cotton, folded tissues, woven materials, nonwoven webs, synthetic and/or natural fibers or sheeting, comminuted wood pulp which is generally referred to as airfelt, or combinations of these materials. Other materials that may be incorporated into the tampon pledget 20 including peat moss, absorbent foams (such as those disclosed in U.S. Pat. No. 3,994,298 issued to DesMarais on Nov. 30, 1976 and U.S. Pat. No. 5,795,921 issued to Dyer, et. al,) capillary channel fibers (such as those disclosed in U.S. Pat. No. 5,356,405 issued to Thompson, et. al on Oct. 18, 1994), high capacity fibers (such as those disclosed in U.S. Pat. No. 4,044,766 issued to Kaczmarzk et al. on Aug. 30, 1977), superabsorbent polymers or absorbent gelling materials (such as those disclosed in U.S. Pat. No. 5,830,543 issued to Miyake, et al on Nov. 3, 1998). A more detailed description of liquid-absorbing materials shapes and dimensions can be found in U.S. patent application Ser. No. 10/039,979, filed Oct. 24, 2001, entitled "Improved Protection and Comfort Tampon," currently pending, and commonly assigned.

The compressed tampon pledget 20 stabilized by the process of the present invention may optionally include an overwrap comprising material such as, rayon, cotton, bicomponent fibers, polyethylene, polypropylene, other suitable natural or synthetic fibers known in the art, and mixtures thereof In some embodiments, the tampon has a nonwoven overwrap comprised of bicomponent fibers that have a polypropylene core surrounded by polyethylene manufactured by Vliesstoffwerke Christian Heinrich Sandler GmbH & Co.KG (Schwarzenbach/Saale, Germany) under the tradename SAS B31812000. In other embodiments, the tampon may comprise a nonwoven overwrap of a hydroentangled blend of 50% rayon, 50% polyester available as BBA 140027 produced by BBA Corporation of South Carolina, U.S. The overwraps may be treated to be hydrophilic, hydrophobic, wicking or non-wicking.

The compressed tampon pledget 20 stabilized by the process of the present invention may optionally include a withdrawal cord, a secondary absorbent member, an additional overwrap, a skirt portion and/or an applicator. Withdrawal cords useful in the present invention may be made of any suitable material known in the prior art and include cotton and rayon. U.S. Pat. No. 6,258,075 to Taylor et al. entitled "Tampon with Enhanced Leakage Protection" describes a variety of secondary absorbent members for use in tampon pledgets 20. An example of a skirt portion is disclosed in U.S. patent application Ser. No. 09/993,988 entitled, "Tampon with Fluid Overwrap with Skirt Portion" currently pending, commonly assigned, and filed on Nov. 16, 2001.

Pressures and temperatures suitable for compression are well known in the art. Typically, the absorbent material and the overwrap are compressed in the radial direction and optionally axially by any means well known in the art. While a variety of techniques are known and acceptable for these purposes, a modified tampon compressor machine available from Hauni Machines, Richmond, Va., is suitable.

The compressed tampon pledget 20 stabilized by the present invention may be inserted digitally or insertion may be aided through the use of any prior art applicators. When the tampons are intended to be digitally inserted, it may be desirable to provide a finger indent made using a compression rod at the withdrawal end of the tampon to aid in insertion. An example of a finger indent is found in U.S. Pat. No. 6,283,952, entitled "Shaped Tampon" issued to Child, et al. on Sep. 4, 2000. Applicators that may be used are "tube and plunger" or "compact" type arrangements and may be plastic, paper, or other suitable material.

Figure 4:
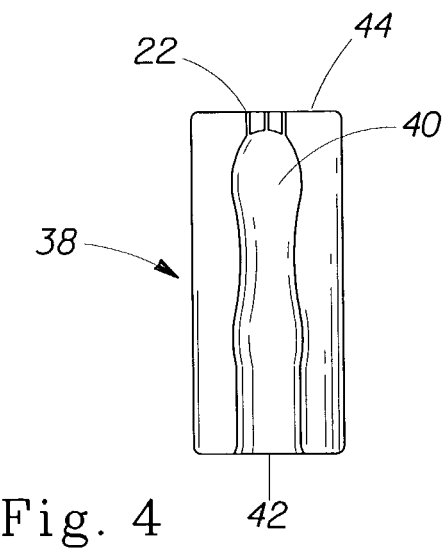
FIG. 4 is a plan view of a first split cavity mold member with pores located axially along the mold.
Figure 5:
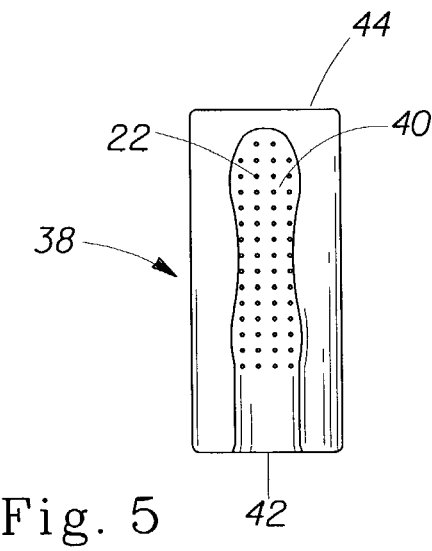
FIG. 5 is a plan view of a first split cavity mold member with pores located radially along the mold.

FIG. 4 and FIG. 5 show plan views of a first split cavity mold member 38 having a first inner surface 40 and an outer mold surface 32 (not shown). The first split cavity mold member 38 has a first end 42 and the second end 44. In the embodiment shown in FIG. 4, the first split cavity mold member 38 has pores 22 located axially along the first split cavity mold member 38. In the embodiment shown in FIG. 5, the first split cavity mold member 38 has pores 22 located radially along the first split cavity mold member 38.

Figure 6:
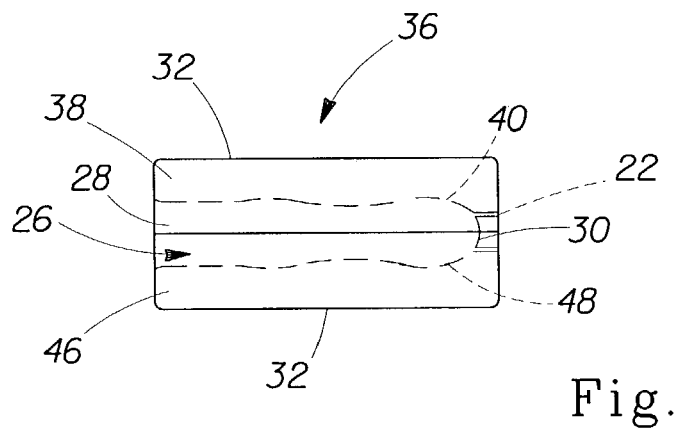
FIG. 6 is a side view of the split cavity mold with pores located axially along the mold.
Figure 7:
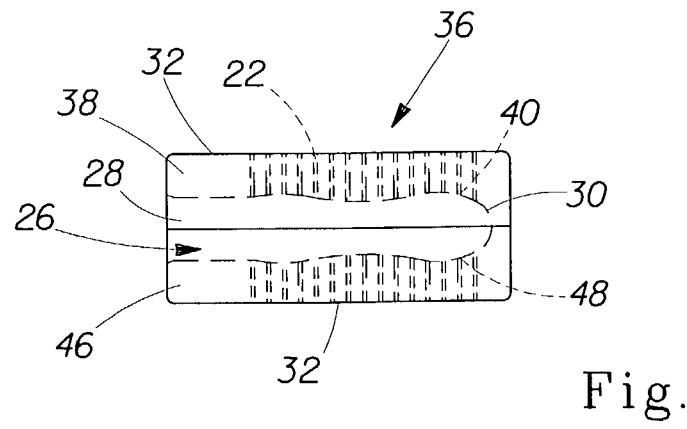
FIG. 7 is a side view of the split cavity mold with pores located radially along the mold.

FIG. 6 and FIG. 7 show a side view of the split cavity mold 36. The first split cavity mold member 38 and second split cavity mold member 46 are combined to form a split cavity mold 36. The first split cavity mold member 38 has a first inner surface 40 and an outer mold surface 32. The second split cavity mold member 46 is substantially similar, if not a mirror image or not identical in size, shape, and dimension to the first split cavity mold member 28 and has a second inner surface 48 and an outer mold surface 32. The first split cavity mold member 38 and the second split cavity mold member 46 are configured, such that, the first inner surface 40 and the second inner surface 48 face toward each other and define an inner cavity 26 for shaping a tampon pledget (not shown) during compression and/or retaining the shape for a compressed tampon pledget subsequent to compression during the stabilization process. The inner cavity 26 has an open proximal end 28 and a closed distal end 30. In some embodiments, such as embodiments that combine compression and stabilization, the open proximal end 28 may act as an ingress port wherein the tampon pledget 20 is introduced in the inner cavity. In the embodiment shown in FIG. 6, the split cavity mold 36 has pores 22 located axially along the split cavity mold 36. In the embodiment shown in FIG. 7, the split cavity mold 36 has pores 22 located radially along the split cavity mold 36.

Figure 8:
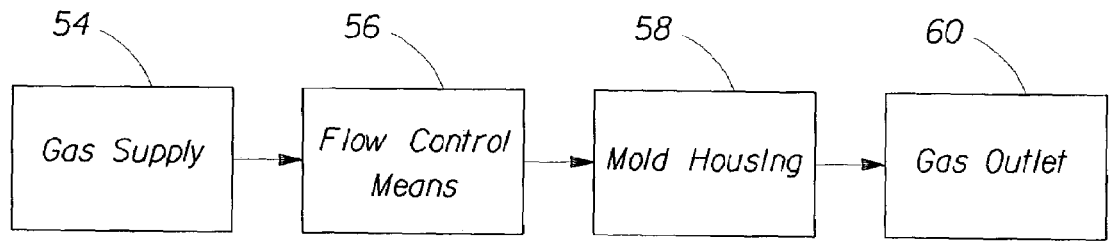
FIG. 8 is a diagram of one embodiment of the process of the present invention
Figure 9:
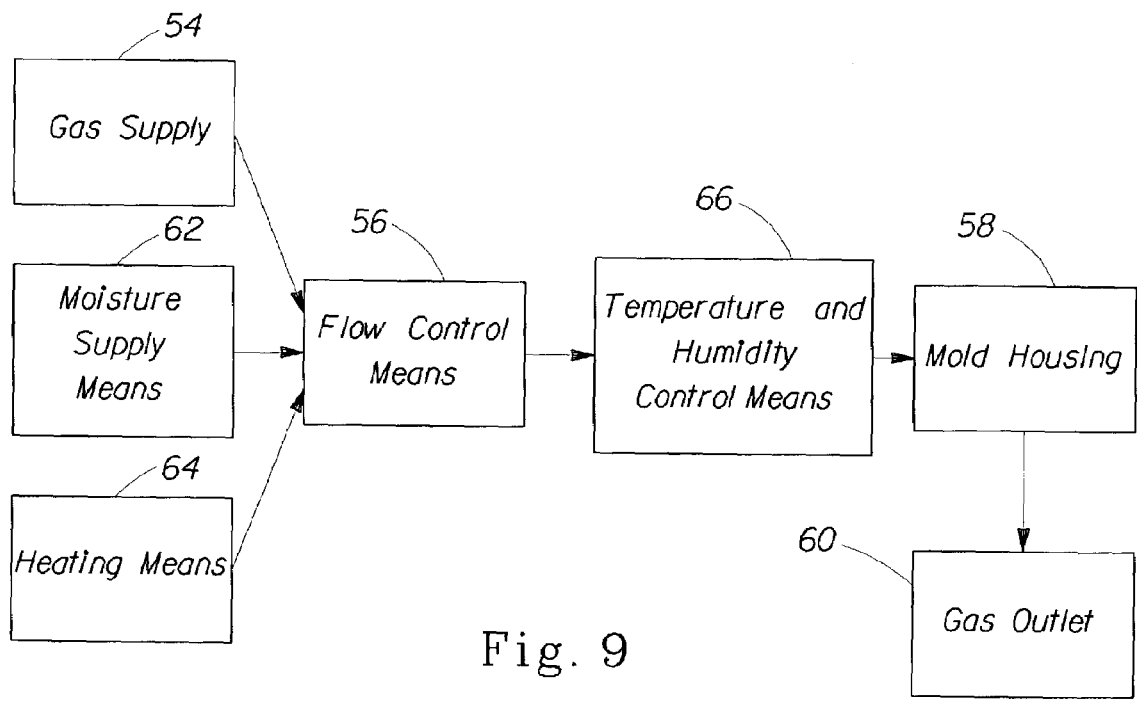
FIG. 9 is a diagram of one embodiment of the process of the present invention

FIG. 8 and FIG. 9 show a flow diagram of the process of the present invention. The process of the present invention comprises the steps of providing a compressed tampon pledget 20 and forcing gas through the compressed tampon pledget. The tampon pledget may be maintained within a permeable mold during this process. In some embodiments of the process, the stabilized compressed tampon may be produced in the presence of moisture. The moisture that is required in the process may be from the fibers of the material that comprises the tampon pledget 20 or within the gas that is introduced in the process or from both the moisture in the tampon pledget 20 and the gas that is introduced. In one embodiment of the process, the tampon pledget 20 that is provided may have an initial moisture content of the gas in the range of from 0 to about 30% water by weight as measured by the TAPPI method T 412, prior to the step of forcing gas through the tampon pledget. In another embodiment of the process, a tampon pledget is provided and the gas that is forced through the tampon pledget is humidified to a range from about 1% to about 100% relative humidity.

In another embodiment of the process, the stabilization process may be combined with a compression process. In these embodiments, the process for producing stabilized compressed tampons comprises the steps of providing a tampon pledget 20, providing a mold, compressing said tampon pledget 20 into the mold, forming a compressed tampon pledget, and forcing a gas into the mold to stabilize the compressed tampon pledget. In some embodiments, the mold provided is permeable. Another variation of this embodiment would be to partially compress the tampon pledget 20 and then have the final compression completed when pushing the tampon pledget 20 into the mold. For example, the process for stabilized tampons may be used in conjunction for the process disclosed in U.S. patent application Ser. No. 10/150049, filed on Mar. 18, 2002, entitled "Method for Producing a Shaped Tampon" currently pending, commonly assigned, and filed on Mar. 18, 2002.

In all embodiments of the present process, the targeted moisture content of the tampon pledget 20 after the stabilization process is from about 4% to about 15% of water by weight, more typically from about 8 to about 10% water by weight as measured by the TAPPI method T 412.

The diagram in FIG. 8 shows that in some embodiments, the process can be accomplished by providing a gas supply 54 opposed to a gas outlet 60, and a mold housing 58 oriented there between that contains the tampon pledget 20 (not shown) within the permeable mold. The incoming gas enters the machine at the gas supply 54. The rate of the gas flow can be varied by a flow control means 56.

The gases forced into the tampon pledget 20 may be air, oxygen, nitrogen, argon, carbon dioxide, steam, ether, freon, inert gases and mixtures thereof. Typically, air is used. One inert gas that may be used to efficiently set the tampon is helium because helium has two times the heat transfer capacity of air. The supply of the gas may be varied by a flow control means 56. During the process of the present invention the gas may be propelled through the mold at a rate from about 0.2 to about 5.0 L/s. In some embodiments, the gas is propelled for time period ranging from about 1 s to about 20 s. In other embodiments, the gas is propelled for a time period ranging from about 1 s to about 10 s. In other embodiments, the gas is propelled from about 2 s to 8 s.

The process of the present invention may comprise the step of heating the gas that is introduced to the tampon pledget. The process of the present invention may comprise the step of humidifying the gas that is introduced to the tampon pledget. As shown in FIG. 9, a moisture supply means 62, heating means 64, and a temperature and humidity control means 66 is added to the diagram of FIG. 8. As such, the heated and humidified gas flows into the mold housing 58 oriented there between that contains the tampon pledget 20 (not shown) within the permeable mold and flows out the gas outlet 60.

In embodiments of the process where the gas is heated, a heating means 64 is used. The temperature may be varied by the temperature and humidity control means 66. In some embodiments, the gas is heated to a range of about 60° C. to about 210° C. In some embodiments, the gas may be heated to 100° C. and in other embodiments the gas may be heated to 163° C. In embodiments where the tampon pledget is maintained in a permeable mold, the molds may be heated prior to insertion of the tampon pledget 20 within the mold. The molds may be heated prior to insertion of the tampon pledget by hot air or alternate means, such as, by conductive heating prior to insertion of the tampon pledget 20. The mold can be heated from about 38° C. to about 210° C. In some embodiments, the molds may be heated to about 71° C. In some embodiments, the process may also comprise the step of cooling the tampon pledget. In some embodiments, the tampon pledget may be cooled by air to ambient room temperatures from about 21 to about 24° C. or less than 30° C.

In embodiments of the process where the gas is humidified, the moisture may be added via a moisture supply means 62. The humidity can be varied by a temperature and humidity control means 66. The moisture or humidity in the gas may be introduced by any know method in the art, including but not limited to atomization, evaporation, steam blending, super heated steam blending, supersaturated steam blending or the like. The gas may be humidified to a range from about 1% to about 100% relative humidity at the gas temperature.

In some embodiments of the process, the gas may be forced intermittently to stabilize the tampon pledget 20. This may include quick pulses of gas flow and includes the "treat" and "hold" method. In the treat and hold method, the tampon pledget 20 within the mold housing 58 is "treated" with gas being propelled through mold, this treatment is followed by a period where the tampon would be "held" within the mold without gas being propelled before the pledget 20 is extracted. In one embodiment of the process, the gas is propelled through the tampon within the mold, the tampon pledget 20 is "held" in the mold without gas being propelled, and gas is then propelled through the tampon again before the tampon pledget 20 is extracted. In another embodiment of the process, gas is propelled through the tampon within the mold, the tampon pledget 20 is "held" in the mold without gas being propelled, and then cool air is propelled through the tampon. In most embodiments of the treat and hold method, the compressed tampon pledget 20 is treated with propelled gas for a time period ranging from about 1 s to about 10 s, or from about 2 s to 8 s. The tampon is held for a time period ranging from about is to about 15 s, or from about 2 s to about 10 s.

As apparent to one skilled in the art, the gas flow rates, temperature, pressure and composition can be varied while holding the tampon pledget in the mold housing 58 to achieve a desired result. For example, the humidity can be changed during the stabilization process. In some embodiments, the process may include a gas control and/or monitoring means to achieve targeted gas condition. Thus, entry and exit gas conditions can be monitored. As well, entry and exit gas conditions may be varied to control the flow, temperature, composition and pressure of the gas flow(s) to achieve a desired result.

The flow of gas can even be reversed either with the same or different gas composition such that the roles of the entry and exit ports are reversed at least for a time. The process may include providing multiple gas supplies 54 and entry ports carrying gases with varied properties including by not limited to different compositions, temperature, flow rate, and pressure. These gas supplies 54 may be employed separately or concurrently. If desired during a portion or the entire process in some embodiments, suction or vacuum can be applied to either assist the flow of gas through the tampon or even lower the pressure in the mold. For example, the pressure inside the mold may be increased above atmospheric pressure for any given duration of time.

Beyond the need for stabilization, the flow of gas can be used to condition the tampon prior, subsequent, or during the stabilization process. Further the gas flow can be used to introduce adjustants into the product. These adjustants can be introduced prior, subsequent, or during the stabilization process. Adjustants may include medicaments, humectants, surface-active agents, lubricants, bactericides, fungicides, spermicides, perfumes, and other adjustants.

EXAMPLE 1

A tampon pledget is made comprising absorbent material and an overwrap. The absorbent material is made of 75% rayon and 25% cotton fiber with a basis weight of 780 g/m$^2$ having dimensions of about 70 mm in width and about 48 mm in length. The overwrap material is made of a nonwoven material comprising a hydroentangled blend of 50% rayon and 50% polyester having dimensions of about 168 mm in width and about 48 mm in length. The tampon pledget is made with a withdrawal means comprising cotton. The tampon pledget is then compressed axially and longitudinally to approximately 14 mm diameter and approximately 46 mm length. The tampon pledget is placed in a permeable mold. The permeable mold is unitary and has plurality of axial pores. The permeable mold containing the tampon pledget is placed in the mold housing of the machine. The air is heated to 100° C. and is humidified to 75% relative humidity. Air is propelled at 3.8 L/s (8 scfm) axially through the tampon pledget for 2 to 30 s. The tampon pledget is then extracted from the permeable mold.

EXAMPLE 2

A shaped tampon pledget is made according to the U.S. patent application Ser. No. 10/150050, entitled "Substantially Serpentine Shaped Tampon." The tampon pledget is made comprising absorbent material and an overwrap. The absorbent material is 75% rayon and 25% cotton fiber with a basis weight of 780 g/m$^2$ having dimensions of about 70 mm in width and about 48 mm in length. The overwrap material is made of a bicomponent fiber having a polypropylene core surrounded by polyethylene having dimensions of about 168 mm in width and about 48 mm in length. The tampon pledget is then compressed axially and longitudinally to form a tampon pledget with a serpentine shape with continually changing cross-sectional areas and diameters along the length of 46 mm in a permeable mold having the same shape. The permeable mold is a split cavity mold that has plurality of radial and axial pores. The permeable mold is placed in the housing of the machine. The air is heated to 100° C. and was humidified to 75% relative humidity. Air is propelled 3.8 L/s (8 scfm) for 2–3 s. The tampon pledget is left in the mold or "held" for 5 s without the gas being propelled through the pledget before the pledget is extracted from the permeable mold.

EXAMPLE 3

A tampon pledget is made comprising absorbent material and an overwrap. The absorbent material is made of 100% GALAXY rayon having the dimensions of about 70 m in width and about 48 mm in length. The overwrap material is made of a nonwoven overwrap comprising a polypropylene core surrounded by polyethylene having dimensions of about 168 mm in width and about 48 mm in length. The tampon pledget is made with a withdrawal means comprising cotton. The tampon pledget is compressed axially and longitudinally to form a tampon pledget of approximately 14 mm diameter and approximately 46 mm length. The tampon pledget is placed in a permeable mold. The permeable mold is unitary and has plurality of axial pores. The permeable mold containing the tampon pledget is placed in the housing of the machine. The gas is heated to 100° C. and is humidified to 75%. Gas is propelled axially at 3.8 L/s (8 scfm) for 2–3 s. The then tampon is left in the mold or "held" for 5 s without the gas being propelled through the pledget.

Cool air is then propelled at 5 s. The gas is cooled to 23° C. and is humidified to 50% relative humidity. The air was propelled for 1–2 s. The pledget is extracted from the mold.

EXAMPLE 4

A tampon pledget is made comprising absorbent material and an overwrap. The absorbent material is made of 75% rayon and 25% cotton fibers with a basis weight of 780 g/m$^2$ having dimension of about 70 mm in width and 48 mm in length. The overwrap is a nonwoven material comprising bicomponent fibers having a polypropylene core surrounded by polyethylene having dimensions of about 168 mm in width and about 48 mm in length. The tampon pledget also comprises a withdrawal means comprising cotton. The tampon pledget is compressed axially and longitudinally to form a tampon pledget of approximately 14 mm diameter and approximately 46 mm length. The tampon pledget is placed in a permeable mold. The permeable mold is a split cavity mold and has a plurality of radial pores. The permeable mold containing the tampon pledget is placed in the housing of the machine. The gas is heated to 100° C. and is humidified to 75% relative humidity. The gas is propelled radially at 3.8 L/s (8 scfm) for 2–3 s. The tampon pledget is then extracted from the permeable mold.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of the invention.

What is claimed is:

1. A process for producing a stabilized compressed tampon, comprising the steps of:
   a. providing a compressed tampon pledget;
   b. stabilizing said compressed tampon pledget by forcing a gas through said compressed tampon pledget while said compressed tampon pledget is maintained in compression.

2. The process according to claim 1, wherein said compressed tampon pledget is maintained within a permeable mold.

3. The process according to claim 2, wherein said mold comprises at least one pore.

4. The process according to claim 1, wherein the gas is selected from the group consisting of air, oxygen, nitrogen, argon, carbon dioxide, steam, ether, freon, inert gases and mixtures thereof.

5. The process according to claim 1 wherein the gas is propelled at rate from about 0.2 to about 4.0 L/s.

6. The process according to claim 1 wherein the gas is forced intermittently to stabilize said compressed tampon pledget.

7. The process according to claim 1 further comprising the step of heating said gas.

8. The process according to claim 1 further comprising the step of humidifying said gas.

9. The process according to claim 1 wherein the gas is humidified to a range from about 1% to about 100% relative humidity.

10. The process according to claim 1 wherein said compressed tampon pledget has a moisture content of 0% to about 30% of water by weight prior to forcing a gas through said compressed tampon pledget.

11. The process according to claim 1, further comprising the step of cooling the tampon pledget.

12. The process according to claim 11, wherein the tampon pledget is cooled with air.

13. A process for producing stabilized compressed tampons, comprising the steps of:
    a. providing a compressed tampon pledget that has a moisture content of 0% to about 30% of water by weight;
    b. stabilizing said compressed tampon pledget by forcing a gas through said compressed tampon pledget while said compressed tampon pledget is maintained in compression.

14. The process according to claim 13 wherein said compressed tampon pledget is maintained within a permeable mold comprising at least one pore.

15. The process according to claim 14 wherein said permeable mold comprises a plurality of pores.

16. A process for producing stabilized compressed tampons, comprising the steps of:
    a. providing a compressed tampon pledget;
    b. stabilizing said compressed tampon pledget by forcing a gas through said compressed tampon pledget while said compressed tampon pledget is maintained in compression, wherein the gas is humidified to a range from about 1% to about 100% relative humidity.

17. The process according to claim 16 wherein the gas is air.

18. The process according to claim 16 wherein the gas is forced intermittently to stabilize said compressed tampon pledget.

19. A process for producing stabilized compressed tampons in the presence of moisture comprising:
    a. providing a tampon pledget;
    b. providing a mold;
    c. compressing said tampon pledget into said mold and forming a compressed tampon pledget;
    d. stabilizing said compressed tampon pledget by forcing a gas into said mold to stabilize said compressed tampon pledget while said compressed tampon pledget is maintained in compression by said mold.

20. A process according to claim 19 wherein the mold is permeable.

* * * * *

UNITED STATES PATENT AND TRADEMARK OFFICE
CERTIFICATE OF CORRECTION

PATENT NO. : 7,124,483 B2 Page 1 of 1
APPLICATION NO. : 10/435822
DATED : October 24, 2006
INVENTOR(S) : Prosise et al.

It is certified that error appears in the above-identified patent and that said Letters Patent is hereby corrected as shown below:

Column 9, line 33, "is" should read --1s--.

Signed and Sealed this

Thirteenth Day of March, 2007

JON W. DUDAS
*Director of the United States Patent and Trademark Office*